United States Patent [19]
Bakshi et al.

[11] Patent Number: 5,278,159
[45] Date of Patent: Jan. 11, 1994

[54] ARYL ESTER DERIVATIVES OF 3-OXO-4-AZA-ANDROSTANE 17-β-CARBOXYLATES AS 5-α-REDUCTASE INHIBITORS

[75] Inventors: Raman K. Bakshi, Edison; Gool F. Patel, Millington; Gary H. Rasmusson, Watchung, all of N.J.

[73] Assignee: Merck & Co., Inc., Rahway, N.J.

[21] Appl. No.: 957,207

[22] Filed: Oct. 6, 1992

[51] Int. Cl.⁵ .................. A61K 31/435; C07D 221/02
[52] U.S. Cl. ........................... 514/232.5; 514/284; 546/77; 544/125
[58] Field of Search ............... 546/77; 514/284, 232.5; 544/125

[56] References Cited

U.S. PATENT DOCUMENTS

| | | | |
|---|---|---|---|
| 2,227,876 | 1/1941 | Bolt | 546/77 |
| 3,239,417 | 3/1966 | DiTullio et al. | 546/77 |
| 3,264,301 | 8/1966 | Doorenboos | 546/77 |
| 3,285,918 | 11/1966 | Doorenboos et al. | 546/77 |
| 4,220,775 | 9/1980 | Rasmusson et al. | 546/77 |
| 4,317,817 | 3/1982 | Blohm et al. | |
| 4,377,584 | 3/1983 | Rasmusson et al. | 514/284 |
| 4,596,812 | 6/1986 | Chidsey, III et al. | |
| 4,732,897 | 3/1988 | Cainelli et al. | 546/77 |
| 4,760,071 | 7/1988 | Rasmusson et al. | 546/77 |
| 4,845,104 | 7/1989 | Carlin et al. | 546/77 |
| 4,859,681 | 8/1989 | Rasmusson et al. | 546/77 |
| 4,882,319 | 11/1989 | Holt et al. | |
| 4,910,226 | 3/1990 | Holt et al. | |
| 5,049,562 | 9/1991 | Rasmusson et al. | 546/77 |
| 5,175,155 | 12/1992 | Juniewicz | 514/284 |

FOREIGN PATENT DOCUMENTS

| | | |
|---|---|---|
| 970692 | 7/1975 | Canada . |
| 0004949 | 10/1979 | European Pat. Off. . |
| 0155096 | 9/1985 | European Pat. Off. . |
| 0200859 | 11/1986 | European Pat. Off. . |
| 0277002 | 6/1988 | European Pat. Off. . |
| 0289327 | 11/1988 | European Pat. Off. . |
| 0314199 | 5/1989 | European Pat. Off. . |
| 0343954 | 11/1989 | European Pat. Off. . |
| 0375344 | 6/1990 | European Pat. Off. . |
| 0375345 | 6/1990 | European Pat. Off. . |
| 0375347 | 6/1990 | European Pat. Off. . |
| 0375349 | 6/1990 | European Pat. Off. . |
| 1465544 | 11/1965 | France . |
| WO91/12261 | 8/1991 | PCT Int'l Appl. . |

OTHER PUBLICATIONS

Stinson, Chem. & Eng. News, Jun. 29, 1992 pp. 7-8.
Helyker, Wall Street Jour. Jun. 7, 1991, pp. A1, A7 (1991).
Endo., vol. 91, No. 2, pp. 427-437 (1972) by Neri, et al., "*A Biological Profile of a Non-steroidal Antiandrogen, SCH 13521* . . . ".
Steroids, 14, 269-283 (1969), by Nayfeh, et al., "*Metabolism of Progesterone by Rat Testicular Homogenates-III*".
J. Pharm. Sci., 62, No. 4, pp. 638-640 (1973) by Doorenbos and Solomons, "*Synthesis & Antimicrobial Properties of 17 Beta-Isopentyloxy-4-Aza-5 Alpha-Androstane and the 4-Methyl Derivative*".
J. Pharm. Sci., 60, No. 8, pp. 1234-1235 (1971) by Doorenbos and Brown, "*4,17 Alpha-Dimethyl-4-Aza-5-Alpha-Androstan-17 beta-ol Acetate & Related Azasteroids*".
J. Pharm., 63, No. 4, pp. 620-622 (1974) by Doorenbos and Kim, "*Synthesis & Evaluation of Antimicrobial Properties of Amidinoazaandrostanes and Guanidinoazaandrostanes*".
J. Med. Chem. (1986) 29 (11): pp. 2298-3015 by Rasmusson, et al., "*Aza Steroids: Structure-Activity Relationships*".
Prostate (1986) 9 (1): pp. 65-75 by Brooks, et al., "*Prostatic Effects Induced in Dogs By . . . 5 alpha-Reductase Inhibitors*".

(List continued on next page.)

Primary Examiner—Donald G. Daus
Attorney, Agent, or Firm—Charles M. Caruso; Robert J. North; Carol S. Quagliato

[57] ABSTRACT

Described are new 17β-aryl ester carboxylates of 4-aza-5α-androstan-3-ones and related compounds and the use of such compounds as 5α-reductase inhibitors for treatment of benign prostatic hyperplasia and other hyperandrogenetic related disorders.

8 Claims, No Drawings

OTHER PUBLICATIONS

Steroids (1986) 47 (1) pp. 1–19 by Brooks, et al., "*5 Alpha-Reductase Inhibitory . . . Activities of Some 4-Aza-Steroids in the rat*".

Endocr. (1985) 117 (2): pp. 571–579, by Liang, et al., "*Species Differences in Prostatic Steroidal 5 Alpha-Reductases of Rat, Dog and Human*".

J. Med. Chem. (1984) 27 (12) pp. 1690–1701, by Rasmusson, et al., "*Azasteroids as Inhibitors of Rat Prostatic 5 alpha-reductase*".

J. Org. Chem. (1981) vol. 46, No. 7, pp. 1442–1446, T. Back, et al., "*N-Chloroazasteroids . . .* ".

Chem. Abstracts, vol. 95, 109055j, by T. Liang, et al. "*Inhibition of 5 Alpha-Receptor Binding . . . by a 4-Methyl-4-Aza-Steroid*" (1981).

JNCI, vol. 74, No. 2, pp. 475–481 (Feb. 1985), by N. Kadohama, et al., "*Retardation of Prostate Tumor Progession in the Noble Rate by 4-Methyl-4-Aza-Steroidal Inhibitors of 5 Alpha-Reductase*".

The Prostate, vol. 10, pp. 189–197 (1987) by G. Andriole, et al., "*The Effect of 4MA . . . on the Growth of . . . Human Tumors . . .* ".

J. Endocr., vol. 57, pp. 111–121 (1973) by K. D. Bingham, et al., "*The Metabolism of Testosterone by Human Male Scalp Skin*".

Toxicol. Appl. Pharmacol., vol. 103, pp. 222–227 (1990) by G. L. Kedderis, et al., "*Studies With Nitrogen Containing Steroids . . .* ".

Bioorganic Chemistry, 17, pp. 372–376 (1986) by B. W. Metacalf, et al., "*Patent Inhibiton of Human Steroid . . . by 3-Androstene-3-Carboxylic Acid*".

Biochemistry, 1990, vol. 29, pp. 2815–2824, by M. A. Levy, et al., "*Inhibition of Rat Liver Steroid 5 Alpha-Reductase . . .* ".

J. Med. Chem., 1990, vol. 33, pp. 943–950, by D. A. Holt, et al. "*Steroidal A Ring Carboxylic Acids . . .* ".

J. Steroid Biochem., vol. 34, Nos. 1–6, pp. 571–575 (1989), by M. A. Levy, et al., "*Interaction Between Rat Prostatic 5 Alpha-Reductase . . .* ".

J. Med. Chem., vol. 33, pp. 937–942 (1990) by D. A. Holt, et al., "*Steroidal A Ring Aryl Carboxylic Acids*".

TIPS, Dec. 1989, vol. 10, pp. 491–495, by D. W. Metcalf, et al., "*Inhibitors of . . . 5 Alpha-Reductase in Benign Prostatic Hyperplasia . . .* ".

Steroids, vol. 35, No. 3 (Mar. 1980) pp. 1–7, by L. Murphy, et al., "*Effect of Estradiol on a . . . Binding Protein in the Uterus of the Mouse*".

Prostate, vol. 9, pp. 311–318 (1986) by N. Stone, et al., "*Estrogen Formation in Human Prostatic Tissue . . .* ".

Steroids, vol. 47, No. 1, pp. 1–19 (1986) by J. R. Brooks, et al., "*5 Alpha-Reductase Inhibitory . . . Activities of Some 4-Azasteroids . . .* ".

Lancet, No. 1986, No. 8515, pp. 1095–1096, by F. Labrie, et al. "*Combination therapy in prostate cancer*".

J. Clin. Endocrin. and Metab., vol. 55, No. 1, pp. 18–193 (1987), by R. Rittmaster, et al., "*The Effects of . . . a 5 Alpha-Reductase Inhibitor . . .* ".

J. Clin. Endocin and Metab., vol. 74, No. 2, pp. 345–350 (1990), by A. Diani, et al., "*Hair Growth Effects of Oral Administration of Finasteride . . .* ".

J. Clin. Endocrinol. Metab. 67, No. 4, pp. 808–816 (1988), by N. Bruchovsky, et al., "*Kinetic Parameters of 5 Alpha-Reductase Activity in Stroma & Epitelium of Normal Hyperplastic & Carcinomatous Human Prostates*".

J. Steroid Biochem. 26, (3) pp. 349–353 (1987), by R. Hudson, "*Comparison of Nuclear 5 Alpha-Reductase Activities in the Stromal and Epitelial Fractions of Human Prostatic Tissue*".

J. Biol. Chem. 251, (19) pp. 5985–5900 (1976), by R. J. Moore, et al., "*Steroid 5 Alpha-Reductase in Cultured Human Fibroblasts*".

J. Biol. Chem. 264, (27) pp. 16249–16255 (1989), by S. Andersson, et al., "*Expression Cloning & Regulation of steroid 5 alpha-Reductase, an Exzyme Essential for Male Sexual Differentiation*".

Proc. Nat'l Acad. Science 87, pp. 3640–3644 (1990), by S. Andersson, et al., "*Structural & Biochemical Properties of cloned and expressed human and rat steroid 5 alpha-reductases*".

Nature 354, pp. 159–161 (Nov. 14, 1991), by S. Andersson, et al., "*Deletion of Steroid 5 Alpha-Reductase-2 Gene in Male Pseudohermaphroditism*".

Biol. of Reproduction, vol. 46, pp. 168–173 (1992), by J. D. Wilson, "*Syndromes of Androgen Resistance*".

Eur. J. Cancer 26 (2), p. 188 (1990) by A. A. Geldof, et al., "*Enzyme Inhibitors in Hormone Dependent Prostate Cancer Growth*".

J. Cancer Res. Clin. Oncol. 118, pp. 50–55 (1992), by A. Geldof, et al., "*Consideration of the Use of . . . 4MA . . . in Prostate Cancer Therapy*".

The Prostate 18, pp. 215–227 (1991), by J. Brooks, et al., "*Effect of Castration, DES, Flutamide, and MK-906 on Growth of the Dunning Rat Prostatic Carcinoma . . .* ".

Eur. J. Pharm. 183 (5), p. 1757 (1990), by Masubuchi, et al., "*Lack of DHT Inhibition . . . by Treatment of 4MA . . .* ".

ARYL ESTER DERIVATIVES OF 3-OXO-4-AZA-ANDROSTANE 17-β-CARBOXYLATES AS 5-α-REDUCTASE INHIBITORS

BACKGROUND OF THE INVENTION

The present invention is directed to new 17β-aryl ester carboxylates of 4-aza-5α-androstan-3-ones and related compounds and the use of such compounds as 5α-reductase inhibitors.

DESCRIPTION OF THE PRIOR ART

The art reveals that certain undesirable physiological manifestations, such as acne vulgaris, seborrhea, female hirsutism, male pattern baldness and benign prostatic hyperplasia, are the result of hyperandrogenetic stimulation caused by an excessive accumulation of testosterone or similar androgenic hormones in the metabolic system. Early attempts to provide a chemotherapeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Non-steroidal antiandrogens have also been developed, for example, 4'-nitro-3'-trifluoromethylisobutyranilide. See Neri, et al., Endo., Vol. 91, No. 2 (1972). However, these products, though devoid of hormonal effects, are peripherally active, competing with the natural androgens for receptor sites, and hence have a tendency to feminize a male host or the male fetus of a female host.

It is now known in the art that the principal mediator of androgenic activity in some target organs, e.g. the prostate, is 5α-dihydrotestosterone, (DHT) and that it is formed locally in the target organ by the action of testosterone-5α-reductase. It is also known that inhibitors of testosterone-5α-reductase will serve to prevent or lessen symptoms of hyperandrogenetic stimulation.

For example, a number of 4-aza steroid compounds are known which are 5α-reductase inhibitors. See the following Merck & Co., Inc. patents, U.S. Pat. Nos. 4,377,584, 4,220,775, 4,859,681, 4,760,071 and the articles J. Med. Chem. 27, p. 1690–1701 (1984) and J. Med. Chem. 29, 2998–2315 (1986) of Rasmusson, et al., and U.S. Pat. No. 4,845,104 to Carlin, et al., and U.S. Pat. No. 4,732,897 to Cainelli, et al. which describe 4-aza-17β-substituted-5α-androstan-3-ones said to be useful in the treatment of DHT-related hyperandrogenic conditions.

Further there is the suggestion in the early prior art that hyperandrogenic diseases are the result of a single 5α-reductase. However, there are later reports regarding the presence of other 5α-reductase isozymes in both rats and humans. For example, in human prostate, Bruchovsky, et al. (See J. Clin. Endocrinol. Metab. 67, 806–816, 1988) and Hudson (see J. Steroid Biochem. 26, p. 349–353, 1987) found different 5α-reductase activities in the stromal and epithelial fractions. Additionally, Moore and Wilson described two distinct human reductases with peaks of activities at either pH 5.5 or pH 7-9. (See J. Biol. Chem. 251, 19, p. 5895–5900, 1976.)

Recently, Andersson and Russell isolated a cDNA which encodes a rat liver 5α-reductase (see J. Biol. Chem. 264 pp. 16249–55 (1989). They found a single mRNA which encodes both the liver and prostatic reductases in rats. This rat gene was later used to identify a human prostatic cDNA encoding a 5α-reductase termed "5α-reductase 1". (See Proc. Nat'l. Acad. Sci. 87, p. 3640–3644, 1990.)

More recently, a second, human prostatic reductase (5α-reductase 2) has been cloned with properties identified with the more abundant form found in crude human prostatic extracts. (See Nature, 354, p. 159–161, 1991.)

Further, "Syndromes of Androgen Resistance"—The Biology of Reproduction, Vol. 46, p. 168–173 (1992) by Jean D. Wilson suggests that the 5α-reductase 1 enzyme is associated with hair follicles.

Thus, the art supports the existence of at least two genes for 5α-reductase and two distinct isozymes of 5α-reductase in humans. Both isozymes are believed to be present in prostatic tissue in which, 5α-reductase 2, is the more abundant, while the other isozyme, 5α-reductase 1, is believed to be more abundant in scalp tissue.

In the treatment of hyperandrogenetic disease conditions, e.g. benign prostatic hyperplasia (BPH) it would be desirable to have one drug entity which is dually active against both enzymes 1 and 2 to substantially inhibit dihydrotesterone (DHT) production. Alternatively, it would be desirable to have a drug entity which is highly selective for inhibiting the scalp-associated enzyme 5α-reductase 1 for treating diseases of the scalp, e.g. androgenic alopecia. This latter drug could also be used in combination with PROSCAR ® (finasteride) which is highly selective for only the prostatic enzyme 5α-reductase 2 for combination therapy in the treatment of BPH.

SUMMARY OF THE INVENTION

The present invention discloses novel 17β-aryl ester carboxylate derivatives of 4-aza-5α-androstan-3-one compounds which are useful for inhibiting the 5α-reductase enzyme and isozymes thereof in prostatic tissue. They are also particularly effective in selectively inhibiting the 5α-reductase 1 associated with the scalp or dually inhibiting both isozymes 1 and 2 in the treatment of benign prostatic hyperplasia, acne, female hirsutism, androgenic alopecia, i.e., male pattern baldness, prostatitis, and the prevention and treatment of prostatic carcinoma.

In accordance with the present invention there is provided novel 17β-aryl ester carboxylates of 4-aza-5α-androstan-3-one and related compounds of the formula:

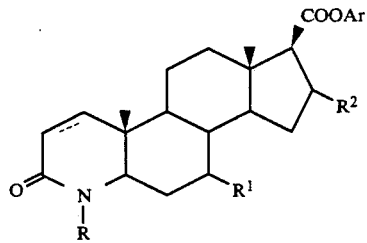

wherein:
the dashed line can represent a double bond when present;
R is selected from hydrogen, methyl, ethyl;
R$^1$ can be:
1) oxo;
2) alpha-hydrogen and beta-hydrogen or a beta-substituent selected from: C$_1$-C$_4$ alkyl, C$_2$-C$_4$ alkenyl, CH$_2$COOH, hydroxy, carboxy, COOC- 1-$C_4$ alkyl esters; $CONR^3R^4$, where $R^3$ and $R^4$ are independently H, $C_1$-$C_4$ alkyl, phenyl, benzyl, and $R^3$ and $R^4$ together with the nitrogen can form a 5-6 membered saturated heterocyclic ring, optionally with one other heteroatom; $OC_1$-$C_4$ alkyl, $OC_3$-$C_6$ cycloalkyl, $OCOCH_3$, halo, hydroxy $C_1$-$C_2$ alkyl, halo $C_1$-$C_2$ alkyl, trifluoromethyl, $C_3$-$C_6$ cycloalkyl;

3) =CH—R' where R' is H, $C_1$-$C_4$ alkyl;

4) spiro:

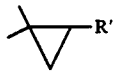

where R' is H, $C_1$-$C_4$ alkyl;

$R^2$ is independently selected from the following alpha and beta substituents: hydrogen, $C_1$-$C_4$ alkyl; and Ar is a $C_6$-$C_{10}$ aromatic ring substituted with one or more of $C_1$-$C_4$ alkyl, $C_1$-$C_4$ alkoxy, or halo;

and pharmaceutically acceptable salts and esters thereof.

Also provided are the new intermediates: 7β-methyl-3-oxo-4-aza-androstane-17β-carboxylic, acid and 7β-methyl-3-oxo-4-aza-androst-1-ene-17β-carboxylic acid.

Also disclosed are processes for their preparation, pharmaceutical formulations comprising the novel compounds as active ingredients and methods of inhibiting 5α-reductases 1 and/or 2 in diseases which occur under hyperandrogenetic conditions, e.g., benign prostatic hyperplasia.

DETAILED DESCRIPTION OF THE INVENTION AND PREFERRED EMBODIMENTS

The structure I above encompasses all the 5α-reductase inhibitor compounds of this invention.

The dashed line can independently be a double bond and when present, the compound is a delta-1-ene.

By the term "$C_1$-$C_4$ alkyl" is meant linear or branched alkyl; e.g. methyl, ethyl, isopropyl, propyl, n-butyl, isobutyl, sec-butyl and the like.

By the term "hydroxy $C_1$-$C_2$ alkyl" is meant monohydroxy $C_1$-$C_2$ alkyl including: hydroxymethyl, 1-hydroxyethyl, 2-hydroxyethyl, and the like.

By the term "halo $C_1$-$C_2$ alkyl" is meant mono halogenated $C_1$-$C_2$ alkyl including: fluoromethyl, chloromethyl, 1-fluoroethyl, 2-fluoroethyl, 1-chloroethyl, 2-chloroethyl, and the like.

By the term "$OC_1$-$C_4$ alkyl" as used herein is meant to include methoxy, ethoxy, propoxy, isopropoxy, n-butoxy, isobutoxy, sec-butoxy, t-butoxy, and the like.

By the term "$OC_3$-$C_6$ cycloalkyl" as used herein is meant to include: cyclopropyloxy, cyclobutyloxy, cyclopentyloxy, cyclohexyloxy, and the like.

Ar is a $C_6$-$C_{10}$ aromatic ring including phenyl, and naphthyl and the like.

$C_2$-$C_4$ alkenyl includes ethenyl, propenyl, 1- and 2-butyryl and the like.

$C_3$-$C_6$ cycloalkyl includes cyclopropyl, cyclobutyl, cyclopentyl, cyclohexyl, and the like.

"Halo" includes fluoro, chloro, bromo and preferred is fluoro, chloro.

$R^3$ and $R^4$ can also be connected to form a 5-6 membered heterocyclic radical, being fully saturated, containing 1-2 nitrogen atoms and 0-1 oxygen atoms, e.g., piperidino, pyrrolidino, morpholino, and the like.

The phenyl and benzyl groups in $R^3$ and $R^4$ can be unsubstituted or substituted with one or more of the following substituents providing the substitution leads to a chemically stable, but biologically active 5-alpha reductase inhibitor:

The ring substituents include:
$C_1$-$C_4$ straight or branched alkyl;
$C_1$-$C_5$ alkoxy; and
halo; all as defined above.

Representative examples of $R^1$ are where the α-substituent (dashed lines) is hydrogen and the beta substituent (wedge) is e.g. methyl, ethyl, propyl, allyl, carboxymethyl, hydroxy, methoxy, ethoxy, cyclopropyloxy, cyclopentyloxy, acetoxy, fluoro, chloro, bromo, trifluoromethyl, trichloromethyl, fluoromethyl, chloromethyl, carboxy, N,N-dimethylcarbamate, hydroxymethyl, methoxymethyl, and the like.

Representative examples where $R^1$ is an alkenyl substituent, =CH—R', includes, e.g. =$CH_2$, =CH—$CH_3$, =CH—$CH_2CH_3$, and the like.

Representative examples where $R^1$ is the spiro substituent:

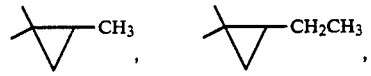

stereoisomers thereof and the like.

Unless otherwise indicated the 17-substituents herein described are assumed to be in the beta configuration.

Representative compounds of the present invention include the following:

2'-Methoxyphenyl-3-oxo-4-methyl-4-aza-5α-androstane-17β-carboxylate

3'-Methoxyphenyl-3-oxo-4-methyl-4-aza-5α-androstane-17β-carboxylate

4'-Methoxyphenyl-3-oxo-4-methyl-4-aza-5α-androstane-17β-carboxylate

2',5'-dimethoxyphenyl-3-oxo-4-methyl-4-aza-5α-androstane-17β-carboxylate

3',4',5'-trimethoxyphenyl-3-oxo-4-methyl-4-aza-5α-androstane-17β-carboxylate

2'-t-Butylphenyl-3-oxo-4-methyl-4-aza-5α-androstane-17β-carboxylate

3'-t-Butylphenyl-3-oxo-4-methyl-4-aza-5α-androstane-17β-carboxylate

4'-t-Butylphenyl-3-oxo-4-methyl-4-aza-5α-androstane-17β-carboxylate

2'-Fluorophenyl-3-oxo-4-methyl-4-aza-5α-androstane-17β-carboxylate

2'-Methoxyphenyl-3-oxo-4-aza-5α-androstane-17β-carboxylate

3'-Methoxyphenyl-3-oxo-4-aza-5'-androstane-17β-carboxylate

4'-Methoxyphenyl-3-oxo-4-aza-5α-androstane-17β-carboxylate

2',6'-Dimethoxyphenyl-3-oxo-4-aza-5α-androstane-17β-carboxylate

3',4',5'-trimethoxyphenyl-3-oxo-4-aza-5α-androstane-17β-carboxylate

2'-t-Butylphenyl-3-oxo-4-aza-5α-androstane-17β-carboxylate

3'-t-Butylphenyl-3-oxo-4-aza-5α-androstane-17β-carboxylate

4'-t-Butylphenyl-3-oxo-4-aza-5α-androstane-17β-carboxylate

2'-Fluorophenyl-3-oxo-4-aza-5α-androstane-17β-carboxylate

2'-Methoxyphenyl-3-oxo-5α-androst-1-ene-17β-carboxylate

3'-Methoxyphenyl-3-oxo-4-aza-5α-androst-1-ene-17β-carboxylate

4'-Methoxyphenyl-3-oxo-4-aza-5α-androst-1-ene-17β-carboxylate

2',6'-dimethoxyphenyl-3-oxo-4-aza-5α-androst-1-ene-17β-carboxylate

3',4',5'-trimethoxyphenyl-3-oxo-4-aza-5α-androst-1-ene-17β-carboxylate

2'-t-Butylphenyl-3-oxo-4-aza-5α-androst-1-ene-17β-carboxylate

3'-t-Butylphenyl-3-oxo-4-aza-5α-androst-1-ene-17β-carboxylate

4'-t-Butylphenyl-3-oxo-4-aza-5α-androst-1-ene-17β-carboxylate

2'-Fluorophenyl-3-oxo-4-aza-5α-androst-1-ene-17β-carboxylate

2'-Methoxyphenyl-3-oxo-4,7β-dimethyl-4-aza-5α-androstane-17β-carboxylate

3'-Methoxyphenyl-3-oxo-4,7β-dimethyl-4-aza-5α-androstane-17β-carboxylate

4'-Methoxyphenyl-3-oxo-7β-ethyl-4-methyl-4-aza-5α-androstane-17β-carboxylate

2',5'-dimethoxyphenyl-3,7-dioxo-4-methyl-4-aza-5α-androstane-17β-carboxylate

3',4',5'-trimethoxyphenyl-4,7β-di-methyl-3-oxo-4-aza-5α-androstane-17β-carboxylate 2'-t-Butylphenyl-4,7β-di-methyl-3-oxo-4-aza-5α-androstane-17β-carboxylate 3'-t-Butylphenyl-4,7β-di-methyl-3-oxo-4-aza-5α-androstane-17β-carboxylate 4'-t-Butylphenyl-4,7β-di-methyl-3-oxo-4-aza-5α-androstane-17β-carboxylate 2'-Fluorophenyl-4,7β-di-methyl-3-oxo-4-aza-5α-androstane-17β-carboxylate 2'-Methoxyphenyl-7β-methyl-3-oxo-4-aza-5α-androstane-17β-carboxylate 3'-Methoxyphenyl-7β-methyl-3-oxo-4-aza-5α-androstane-17β-carboxylate 4'-Methoxyphenyl-7β-methyl-3-oxo-4-aza-5α-androstane-17β-carboxylate 2',6'-Dimethoxyphenyl-7β-methyl-3-oxo-4-aza-5α-androstane-17β-carboxylate 3',4',5'-trimethoxyphenyl-7β-methyl-3-oxo-4-aza-5α-androstane-17β-carboxylate 2'-t-Butylphenyl-3,7-di-oxo-4-aza-5α-androstane-17β-carboxylate 3'-t-Butylphenyl-3,7-di-oxo-4-aza-5α-androstane-17β-carboxylate 4'-t-Butylphenyl-3,7-di-oxo4-aza-5α-androstane-17β-carboxylate 2'-Fluorophenyl-3,7-di-oxo-4-aza-5α-androstane-17β-carboxylate 2'-Methoxyphenyl-7β-ethyl-3-oxo-4-aza-5α-androst-1-ene-17β-carboxylate 3'-Methoxyphenyl-7β-ethyl-3-oxo-4-aza-5α-androst-1-ene-17β-carboxylate 4'-Methoxyphenyl-7β-ethyl-3-oxo-4-aza-5α-androst-1-ene-17β-carboxylate 2',6'-dimethoxyphenyl-7-fluoro-3-oxo-4-aza-5α-androst-1-ene-17β-carboxylate 3',4',5'-trimethoxyphenyl-7β-propyl-3-oxo-4-aza-5α-androst-1-ene-17β-carboxylate 2'-t-Butylphenyl-7-methylene-3-oxo-4-aza-5α-androst-1-ene-17β-carboxylate 3'-t-Butylphenyl-7-methylene-3-oxo-4-aza-5α-androst-1-ene-17β-carboxylate 4'-t-Butylphenyl-7-methylene-3-oxo-4-aza-5α-androst-1-ene-17β-carboxylate 2'-Fluorophenyl-7-methylene-3-oxo-4-aza-5α-androst-1-ene-17β-carboxylate and also including the corresponding compounds wherein the 4-hydrogen substituent is replaced by a methyl or an ethyl radical, and a delta-one double bond is present or absent.

Also included within the scope of this invention are pharmaceutically acceptable salts, i.e. hydrochloride, hydrobromide, acetate, pamoate, and the like, which can be used as the dosage form for modifying solubility or hydrolysis characteristics or for use as sustained release or prodrug formulations.

The novel compounds of formula I of the present invention are prepared by methods discussed below. The compounds and intermediates, their physical properties, and their preparation is illustrated in Examples 1–30.

The starting materials for these preparations are:

A; 4-methyl-3-oxo-4-aza-5α-androstane-17-carboxylic acid, whose preparation is described in J. Med. Chem. Vol. 27, p. 1690–1701 (1984);

B; 3-oxo-4-aza-5α-androstane-17-carboxylic acid, whose preparation is described in J. Med. Chem. Vol. 29, p. 2998–2315 (1986);

C; 3-oxo-4-aza-5α-androst-1-ene-17β-carboxylic acid, whose preparation is described in J. Med. Chem. Vol. 29, p. 2998–2315 (1986);

D; 7β-methyl-3-oxo-5a-4-aza-androstane-17b-carboxylic acid,

E; 4,7β-dimethyl-3-oxo-4-aza-5a-androstane-17b-carboxylic acid,

F; 4,7β-dimethyl-3-oxo-4-aza-5a-androstane-1-ene-17b-carboxylic acid,

G; 7β-methyl-3-oxo-4-aza-5α-androst-1-ene-17β-carboxylic acid,

H; 4-methyl-3,7-dioxo-4-aza-5α-androstane-17β-carboxylic acid,

I; 3,7-dioxo-4-aza-5α-androstane-17β-carboxylic acid,

J; 7-methoxycarbonylmethyl-4-methyl-3-oxo-4-aza-5α-androstane-17β-carboxylic acid, K; 7-allyl-4-methyl-3-oxo-4-aza-5α-androstane-17β-carboxylic acid, Other starting materials can be prepared from the above intermediates by selective 4-N-alkylation, introduction of the 1,2-double bond as described in the above J. Med. Chem. references and by derivitization of the 7-oxo substituent by suitable methods.

Scheme 1
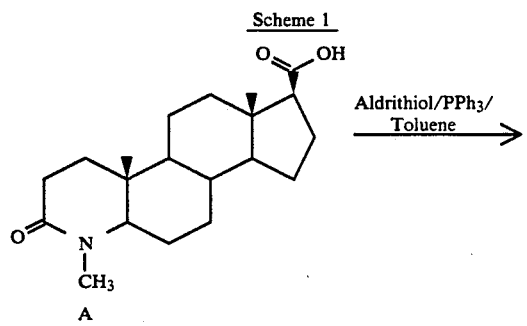
A
Aldrithiol/PPh₃/Toluene →
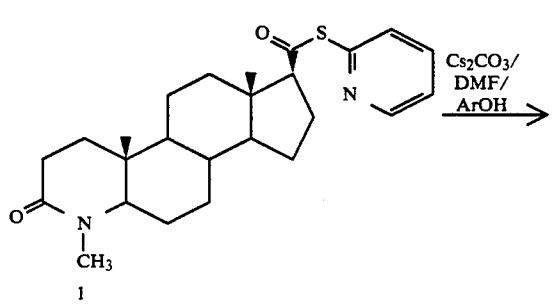
1
Cs₂CO₃/DMF/ArOH →
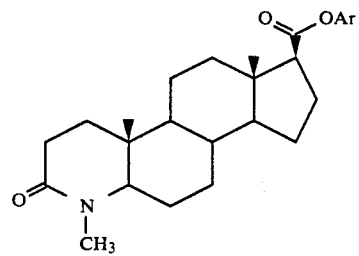
Compounds prepared by this scheme are as follows:
Ar
2 = 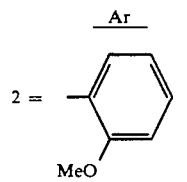 MeO
3 = 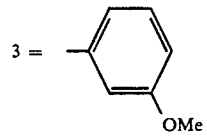 OMe
4 = 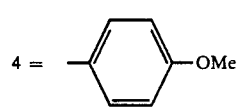 OMe
5 = 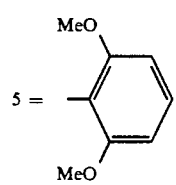 MeO / MeO
-continued
Ar
6 = 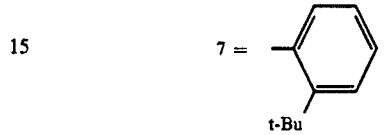 OMe / OMe / OMe
7 = 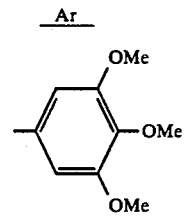 t-Bu
8 = 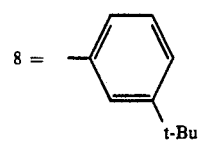 t-Bu
9 = 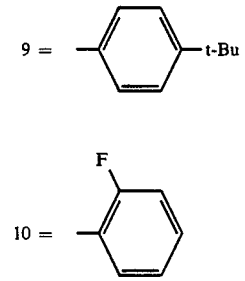 t-Bu
10 = F
Scheme 2
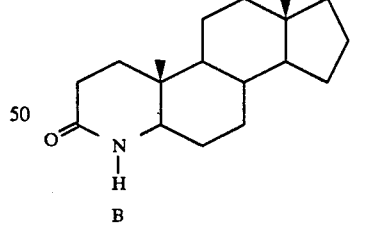
B
Aldrithiol/PPh₃/Toluene →
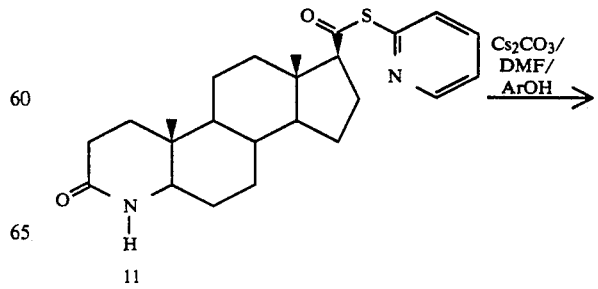
11
Cs₂CO₃/DMF/ArOH →

-continued
Scheme 2
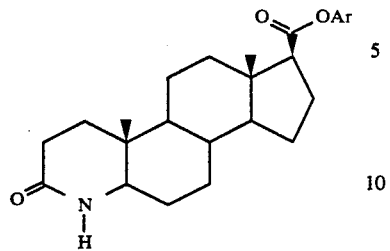
Compounds prepared by this scheme are as follows:
| | Ar |
|---|---|
| 12 = | 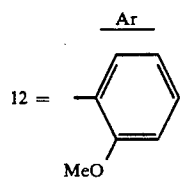 |
| 13 = | 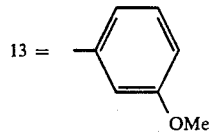 |
| 14 = | 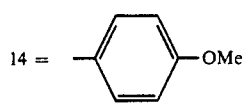 |
| 15 = | 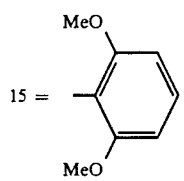 |
| 16 = | 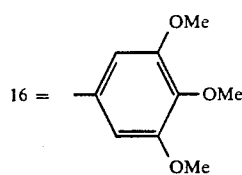 |
| 17 = | 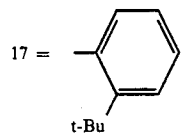 |
| 18 = | 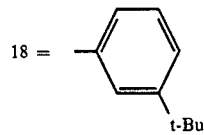 |
| 19 = | 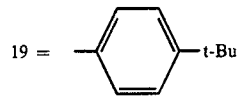 |
-continued
| | Ar |
|---|---|
| 20 = | 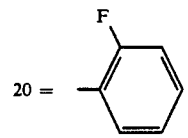 |
Scheme 3
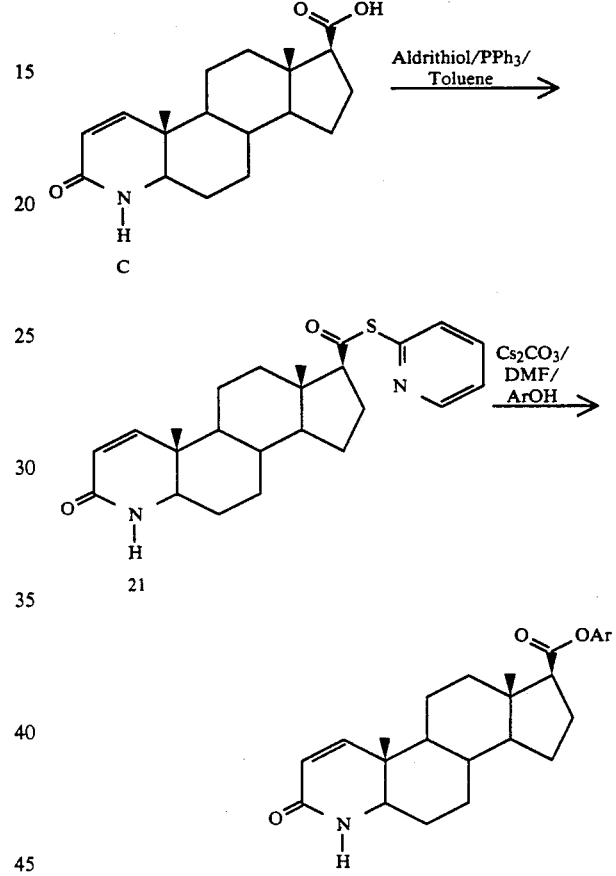
Compounds prepared by this scheme are as follows:
| | Ar |
|---|---|
| 22 = | 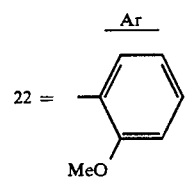 |
| 23 = | 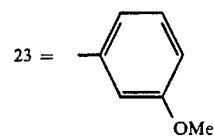 |
| 24 = | 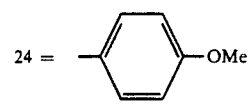 |

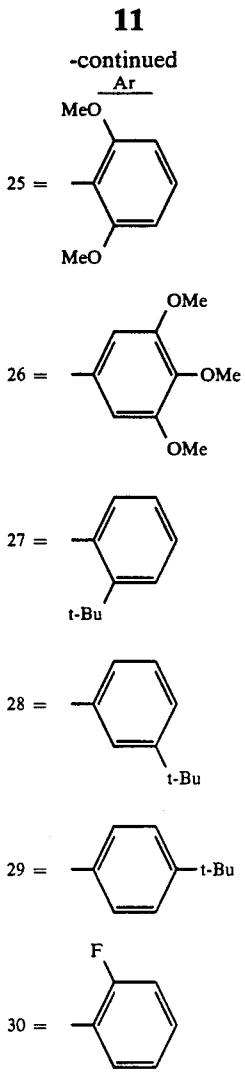

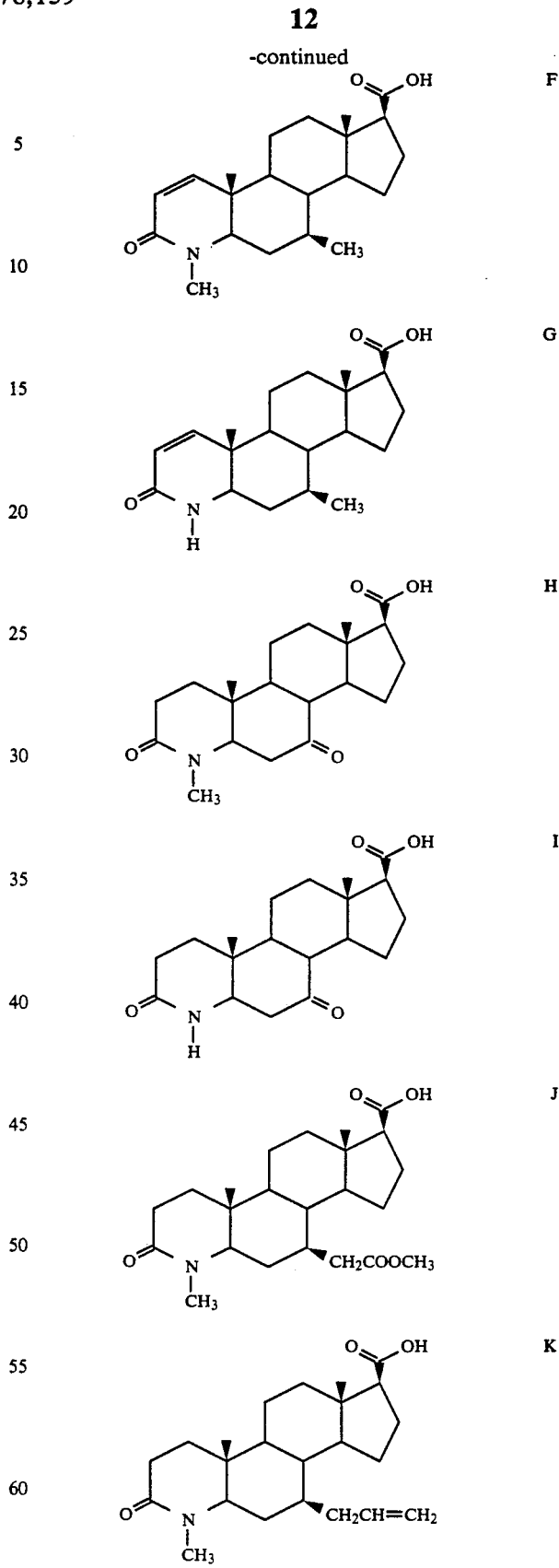

The compounds of the instant invention where R' is other than hydrogen are made by carrying out Reaction Schemes 1-3 but utilizing the following 7-substituted azasteroid intermediates D-K. In general, the 7-substituent is formed first on the intermediate, then reacted with the appropriate phenol to form the 17-acylester.

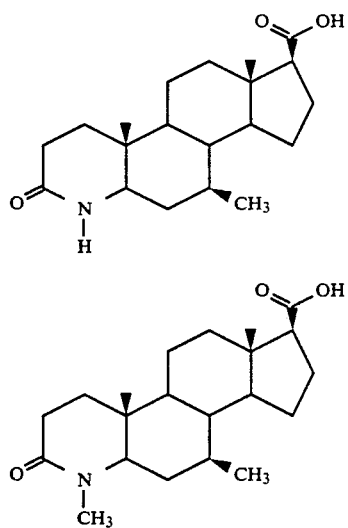

The compounds of the invention are produced by the Reaction Schemes 1-3 shown above.

The starting carboxylic acid A, B or C is first reacted with 2-pyridylthiol and triphenylphosphine in toluene overnight at room temperature (r.t.) to produce the corresponding 2-pyridyl-thio keto analogues (e.g. 1, 11, 21).

This thio derivative is then reacted with a displacing substituted phenol, e.g. ArOH, in dimethylformamide containing cesium carbonate as catalyst at room temperature over a 4 hour period to yield the new 17-beta-substituted aryl ester.

Conventional isolation and purification procedures, e.g., chromatography, fractional crystallization yields the pure product.

Representative examples of phenols used are 2-methoxyphenol, 3-methoxyphenol, 4-methoxyphenol, 2,6-di-methoxyphenol, 3,4,5-trimethoxyphenol, 2-(t-butyl)phenol, 3-(t-butyl)phenol, 4-(t-butyl)-phenol, and 2-fluorophenol, and the like.

Accordingly, the present invention is particularly concerned with providing a method of treating the hyperandrogenic conditions of acne vulgaris, seborrhea, female hirsutism as well as benign prostatic hyperplasia, prostatitis, and prostatic carcinoma by oral or parenteral administration of the novel compounds of the present invention.

The present invention is thus also concerned with providing suitable topical, oral and parenteral pharmaceutical formulations for use in the novel methods of treatment of the present invention.

The compositions containing the compounds of the present invention as the active ingredient for use in the treatment of benign prostatic hypertrophy can be administered in a wide variety of therapeutic dosage forms in conventional vehicles for systemic administration, as, for example, by oral administration in the form of tablets, capsules, solutions, or suspensions, of by intravenous injection. The daily dosage of the products for an adult human/per day may be varied over a wide range varying from 0.5 to 1,000 mg. The compositions are preferably provided in the form of scored tablets containing 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.002 mg. to about 50 mg./kg. of body weight per day. Preferably the range is from about 0.01 mg. to 7 mg./kgs. of body weight per day. These dosages are well below the toxic dose of the product. Capsules containing the product of this invention can be prepared by mixing an active compound of the present invention with lactose and magnesium stearate, calcium stearate, starch, talc, or other carriers, and placing the mixture in gelatin capsule. Tablets may be prepared by mixing the active ingredient with conventional tableting ingredients such as calcium phosphate, lactose, corn starch or magnesium stearate. The liquid forms in suitably flavored suspending or dispersing agents such as the synthetic and natural gums, for example, tragacanth, acacia, methylcellulose and the like. Other dispersing agents which may be employed include glycerin and the like. For parenteral administration, sterile suspensions and solutions are desired. Isotonic preparations which generally contain suitable preservative are employed when intravenous administration is desired.

For the treatment of acne vulgaris, seborrhea, female hirsutism, the compounds of the present invention are administered in the formula of pharmaceutical composition comprising the active compound in combination with a pharmacologically acceptable carrier adapted for topical administration. Parenteral administration is also applicable. These topical pharmaceutical compositions may be in the form of a cream, ointment, gel or aerosol formulation adapted for application to the skin. These topical pharmaceutical compositions containing the compounds of the present invention ordinarily include about 0.1% to 15%, preferably about 5%, of the active compound, in admixture with about 95% of vehicle.

The methods of preparing the novel 17$\beta$-aryl ester, derivatives of 3-oxo-4-azasteroids of the present invention, already described above in general terms, may be further illustrated by the following examples.

EXAMPLE 1

S-2'-pyridyl-3-oxo-4-aza-4-methyl-5$\alpha$-androstane-17$\beta$-thiocarboxylate.(intermediate) (1)

To a solution of 3-oxo-4-methyl-4-aza-5$\alpha$-androstane-17$\beta$-carboxylic acid (7.0 g, 21 mmol) in toluene (300 ml) was added Aldrithiol * (14.7 g, 66.7 mmol) and triphenylphosphine (16.49 g, 62.8 mmol). After stirring the reaction mixture for overnight at room temperature, the reaction mixture was concentrated under vacuum and purified by column chromatography over silica gel using 10% acetone/methylene chloride to give 6.0 g of titled pure product 1.

*Commercially available from the Aldrich Chemical Co.

EXAMPLE 2

2'-Methoxyphenyl-3-oxo-4-methyl-4-aza-5$\alpha$-androstane-17$\beta$-carboxylate (2)

To a solution of S-2'-pyridyl-3-oxo-4-methyl-4-aza-5$\alpha$-androstane-17$\beta$-thiocarboxylate (200 mg, 0.47 mmol) in DMF was added $Cs_2CO_3$ (326 mg, 1 mmol) and guaiacol (125 $\mu$l, 1.13 mmol). After stirring the reaction mixture for 4 hrs, the reaction mixture was diluted with water and extracted with methylene chloride. The organic layer was dried, concentrated, residue purified by HPLC using Partisil M9 10/50 column and 30% acetone/methylene chloride as solvent to give desired titled product 2, Mp195°–197° C. Mass spec. (MS) M+ calculated, 439.58; observed m/e 439 (EI). Anal. calcd for $C_{27}H_{37}NO_4 \cdot 0.3H_2O$, C 72.87; H 8.50; N 3.14. Found: C 72.79; H 8.54; N 3.05.

EXAMPLE 3

3'-Methoxyphenyl-3-oxo-4-aza-4-methyl-5$\alpha$-androstane-17$\beta$-carboxylate (3)

Employing substantially the same procedure as described in Example 2, but substituting the guaiacol with 3-methoxyphenol, the titled product 3 was obtained. Mp 196°–198° C. Mass spec. (MS) calculated 439.58; observed m/e 439. Anal. calcd. for $C_{27}H_{37}NO_4 \cdot 0.3H_2O$, C 72.87; H 8.50; N 3.4. Found C 72.87; H 8.68; N 3.05.

EXAMPLE 4

4'-Methoxyphenyl-3-oxo-4-aza-4-methyl-5$\alpha$-androstane-17$\beta$-carboxylate (4)

Employing substantially the same procedure as described in Example 2, but substituting the guaiacol with 4-methoxyphenol, the titled product 4 was obtained. Mp 148°–150° C. Mass spec. (MS) calculated, 439.58; observed m/e 439. Anal. calcd. for $C_{27}H_{37}NO_4$, C 73.76; H 8.48; N 3.31. Found C 73.52; H 8.31; N 3.12.

EXAMPLE 5

2',5'-dimethoxyphenyl-3-oxo-4-methyl-4-aza-5α-androstane-17β-carboxylate (5)

Employing substantially the same procedure as described in Example 2, but substituting the guaiacol with 2,5-dimethoxyphenol, the titled product 5 was obtained. Mp 161°–162° C. Mass spec. (MS) calculated, 469.60; observed m/e 469. Anal. calcd. $C_{28}H_{39}NO_5 \bullet 0.3H_2O$, C 70.82; H 8.43; N 2.85. Found C 70.82; H 8.43; N 2.95.

EXAMPLE 6

3',4',5'-trimethoxyphenyl-3-oxo-4-methyl-4-aza-5α-androstane-17β-carboxylate (6)

Employing substantially the same procedure as described in Example 2, but substituting the guaiacol with 3,4,5-triimethoxyphenol, the titled product 6 was obtained. Mp 133°–135° C. Mass spec. (MS) calculated, 499.63; observed m/e 499. Anal. calcd. $C_{29}H_{41}NO_6 \bullet 0.3H_2O$, C 68.96; H 8.30; N 2.77. Found C 68.94; H 8.29; N 2.70.

EXAMPLE 7

2'-t-Butylphenyl-3-oxo-4-methyl-4-aza-5α-androstane-17β-carboxylate (7)

Employing substantially the same procedure as described in Example 2, but substituting the guaiacol with 2-t-butylphenol, the titled product 7 was obtained. Mp 133°–135° C. Mass spec. (MS) calculated, 465.68; observed m/e 465. Anal. calcd. for $C_{30}H_{43}NO_3$, C 77.38; H 9.31; N 3.01. Found C 77.35; H 9.63; N 2.90.

EXAMPLE 8

3'-t-Butylphenyl-3-oxo-4-methyl-4-aza-5α-androstane-17β-carboxylate (8)

Employing substantially the same procedure as described in Example 2, but substituting the guaiacol with 3-t-butylphenol, the titled product 8 was obtained, Mp 135°–136° C. Mass spec. (MS) calculated, 465.68; observed m/e 465. Anal. calcd. for $C_{30}H_{43}NO_3 \bullet 0.4H_2O$, C 76.20; H 9.34; N 2.96. Found C 76.17; H 9.07; N 3.05.

EXAMPLE 9

4'-t-Butylphenyl-3-oxo-4-methyl-4-aza-5α-androstane-17β-carboxylate (9)

Employing substantially the same procedure as described in Example 2, but substituting the guaiacol with 4-t-butylphenol, the titled product 9 was obtained. Mass spec. (MS) calculated, 465.68; observed m/e 465. Anal. calcd. for $C_{30}H_{43}NO_3$, C 77.38; H 9.31; N 3.01. Found C 77.46; H 9.40; N 2.91.

EXAMPLE 10

2'-Fluorophenyl-3-oxo-4-methyl-4-aza-5α-androstane-17β-carboxylate (10)

Employing substantially the same procedure as described in Example 2, but substituting the guaiacol with 2-t-fluorophenol, the titled product 10 was obtained. Mass spec. (MS) calculated, 427.54; observed m/e 427. Anal. calcd. for $C_{26}H_{34}NO_3F$, C 73.04; H 8.01; N 3.28. Found C 72.79; H 8.05; N 3.09.

EXAMPLE 11

S-2'-pyridyl-3-oxo-4-aza-5α-androstane-17β-thiocarboxylate (11, intermediate)

To a solution of 3-oxo-4-aza-5α-androstane-17β-carboxylic acid (20.0 g, 62.7 mmol) in toluene (120 ml) was added aldrithiol (28 g, 127 mmol) and triphenylphosphine (32 g, 122 mmol). After stirring the reaction mixture for overnight at room temperature, the titled product 11 precipitated out of solution and was filtered (20 g), Mp 247°–249° C.

EXAMPLE 12

2'-Methoxyphenyl-3-oxo-4-aza-5α-androstane-17β-carboxylate (12)

To a solution of S-2'-pyridyl-3-oxo-4-aza-5α-androstane-17β-thiocarboxylate (207 mg, 0.5 mmol) in DMF (10 ml) was added $Cs_2CO_3$ (326 mg, 1 mmol) and guaiacol (125 ml, 1.13 mmol). After stirring the reaction mixture for 4 hrs, the reaction mixture was diluted with water and extracted with methylene chloride. The organic layer was dried, concentrated, residue purified by prep. silica gel tlc (3:1 acetone/methylene chloride) and recrystallized from ether, to yield the above titled product 12, Mp 228°–230° C. Mass spec. (MS) M+ calculated, 425.55; observed m/e 425 (EI). Anal. calcd for $C_{26}H_{35}NO_4 \bullet 0.2H_2O$, C 72.76; H 8.31; N 3.26. Found: C 72.783; H 8.23; N 3.17.

EXAMPLE 13

3'-Methoxyphenyl-3-oxo-4-aza-5α-androstane-17β-carboxylate (13)

Employing substantially the same procedure as described in Example 12, but substituting the guaiacol with 3-methoxyphenol, yields the titled product 13. Mp 216°–217° C. Mass spec. (MS) calculated, 425.57; observed m/e 425. Anal. calcd. for $C_{26}H_{35}NO_4 \bullet 0.2H_2O$, C 72.76; H 8.31; N 3.26. Found C 72.71; H 8.22; N 3.28.

EXAMPLE 14

4'-Methoxyphenyl-3-oxo-4-aza-5α-androstane-17β-carboxylate (14)

Employing substantially the same procedure as described in Example 12, but substituting the guaiacol with 4-methoxyphenol, the titled product 14 is obtained, Mp 299°–301° C. Mass spec. (MS) calculated, 425.57; observed m/e 425. Anal. calcd. for $C_{26}H_{35}NO_4$, C 73.38; H 8.29; N 3.29. Found C 72.91; H 8.23; N 3.29.

EXAMPLE 15

2',6'-Dimethoxyphenyl-3-oxo-4-aza-5α-androstane-17β-carboxylate (15)

Employing substantially the same procedure as described in Example 12, but substituting the guaiacol with 2,6-dimethoxyphenol, the titled product 15 is obtained. Mp 256°–58° C. Mass spec. (MS) calculated, 455.599; observed m/e 455. Anal. calcd. for $C_{27}H_{37}NO_5$, C 71.18; H 8.19; N 3.08. Found C 71.06; H 8.28; N 2.96.

EXAMPLE 16

3',4',5'-trimethoxyphenyl-3-oxo-4-aza-5α-androstane-17β-carboxylate (16)

Employing substantially the same procedure as described in Example 12, but substituting the guaiacol with 3,4,5-trimethoxyphenol, the titled product 16 is obtained. Mp 244°–246° C. Mass spec. (MS) calculated, 485.60; observed m/e 485.

EXAMPLE 17

2'-t-Butylphenyl-3-oxo-4-aza-5α-androstane-17β-carboxylate (17)

Employing substantially the same procedure as described in Example 12, but substituting the guaiacol with 2-t-butylphenol, the title product 17 is obtained. Mp 189°–91° C. Mass spec. (MS) calculated, 451.63; observed m/e 451. Anal. calcd. for $C_{29}H_{41}NO_3$, C 77.11; H 9.15; N 3.10. Found C 76.89; H9.35; N 3.01.

EXAMPLE 18

3'-t-Butylphenyl-3-oxo-4-aza-5α-androstane-17β-carboxylate (18)

Employing substantially the same procedure as described in Example 12, but substituting the guaiacol with 3-t-butylphenol, the titled product 18 is obtained. Mp 228°–231° C. Mass spec. (MS) calculated, 451.63; observed m/e 451. Anal. calcd. for $C_{29}H_{41}NO_3$, C 77.11; H 9.15; N 3.10. Found C 77.09; H9.25; N 3.09.

EXAMPLE 19

4'-t-Butylphenyl-3-oxo-4-aza-5α-androstane-17β-carboxylate (19)

Employing substantially the same procedure as described in Example 12, but substituting the guaiacol with 4-t-butylphenol, the titled product 19 is obtained. Mass spec. (MS) calculated, 451.63; observed m/e 451. Anal. calcd. for $C_{29}H_{41}NO_3$, C 77.11; H 9.15; N 3.11. Found C 76.94; H9.16; N 3.04.

EXAMPLE 20

2'-Fluorophenyl-3-oxo-4-aza-5α-androstane-17β-carboxylate (20)

Employing substantially the same procedure as described in Example 12, but substituting the guaiacol with 2-fluorophenol, the titled product 20 is obtained. Mass spec. (MS) calculated, 413.52; observed m/e 302 (m-111). Anal. calcd. for $C_{25}H_{32}NO_3F \cdot 0.2H_2O$, C 71.98; H 7.82; N 3.35. Found C 71.99; H 7.87; N 3.42.

EXAMPLE 21

S-2'-pyridyl-3-oxo-4-aza-5α-androst-1-ene-17β-thiocarboxylate (21, intermediate)

To a solution of 3-oxo-4-aza-5α-androst-1-ene-17β-carboxylic acid (10.0 g, 31.5 mmol) in toluene (60 ml) was added aldrithiol (14 g, 63.5 mmol) and triphenylphosphine (316 g, 61 mmol). After stirring the reaction mixture for overnight at room temperature, the titled product 21 precipitated out of solution and was filtered (8.4 g).

EXAMPLE 22

2'-Methoxyphenyl-3-oxo-4-aza-5α-androst-1-ene-17β-carboxylate (22)

To a solution of S-2'-pyridyl-3-oxo-4-aza-5α-androst-1-ene-17β-thiocarboxylate (205 mg, 0.5 mmol) in DMF (10 ml) was added $Cs_2CO_3$ (326 mg, 1 mmol) and guaiacol (125 ml, 1.13 mmol). After stirring the reaction mixture for 4 hrs, the reaction mixture was diluted with water and extracted with methylene chloride. The organic layer was dried, concentrated, residue purified by prep. silica gel tlc (3:1 acetone/methylene chloride) and recrystallized from ether, to yield the titled product 22. Mp 247°–249° C. Mass spec. (MS) M+ calculated, 423.53; observed m/e 423 (EI). Anal. calcd for $C_{26}H_{33}NO_4 \cdot 0.2H_2O$, C 73.08; H 7.75; N 3.18. Found: C 73.10; H 7.88; N 3.38.

EXAMPLE 23

3'-Methoxyphenyl-3-oxo-4-aza-5α-androst-1-ene-17β-carboxylate (23)

Employing substantially the same procedure as described in Example 22, but substituting the guaiacol with 3-methoxyphenol, the titled product 23 is obtained. Mp 223°–229° C. Mass spec. (MS) calculated, 423.53; observed m/e 423. Anal. calcd. for $C_{26}H_{33}NO_4 \cdot 0.6H_2O$, C 71.58; H 7.64; N 3.13. Found: C 71.89; H 7.93; N 3.23.

EXAMPLE 24

4'-Methoxyphenyl-3-oxo-4-aza-5α-androst-1-ene-17β-carboxylate (24)

Employing substantially the same procedure as described in Example 22, but substituting the guaiacol with 4-methoxyphenol, the titled product 24 was obtained. Mp 302°–304° C. Mass spec. (MS) calculated, 423.53; observed m/e 423. Anal. calcd. for $C_{26}H_{33}NO_4 \cdot 0.3H_2O$, C 72.80; H 7.90; N 3.27. Found C 72.88; H 7.90; N 3.13.

EXAMPLE 25

2',6'-dimethoxyphenyl-3-oxo-4-aza-5α-androst-1-ene-17β-carboxylate (25)

Employing substantially the same procedure as described in Example 22, but substituting the guaiacol with 2,6-dimethoxyphenol, the titled product 25 was obtained. Mp 259°–261° C. Mass spec. (MS) calculated, 453.58; observed m/e 453. Anal. calcd. for $C_{27}H_{35}NO_5$, C 71.49; H 7.78; N 3.09. Found C 71.10; H 7.72; N 2.84.

EXAMPLE 26

3',4',5'-trimethoxyphenyl-3-oxo-4-aza-5α-androst-1-ene-17β-carboxylate (26)

Employing substantially the same procedure as described in Example 22, but substituting the guaiacol with 3,4,5-trimethoxyphenol, the titled product 26 was obtained. Mp 238°–239° C. Mass spec. (MS) calculated, 483.59; observed m/e 483. Anal. calcd. for $C_{28}H_{37}NO_6 \cdot 0.3H_2O$, C 68.77; H 7.75; N 2.87. Found C 68.81; H 7.49; N 2.92.

EXAMPLE 27

2'-t-Butylphenyl-3-oxo-4-aza-5α-androst-1-ene-17β-carboxylate (27)

Employing substantially the same procedure as described in Example 22, but substituting the guaiacol with 2-t-butylphenol, the titled product 27 was obtained. Mp 229°–231° C. Mass spec. (MS) calculated, 449.61; observed m/e 449. Anal. calcd. for $C_{29}H_{39}NO_3 \cdot 0.3H_2O$, C 77.46; H 8.74; N 3.12. Found C 76.53; H 8.61; N 3.03.

EXAMPLE 28

3'-t-Butylphenyl-3-oxo-4-aza-5α-androst-1-ene-17β-carboxylate (28)

Employing substantially the same procedure as described in Example 22, but substituting the guaiacol with 3-t-butylphenol, the titled product 28 was obtained. Mp 222°-225° C. Mass spec. (MS) calculated, 449.61; observed m/e 449. Anal. calcd. for $C_{29}H_{39}NO_3\cdot 0.3H_2O$, C 76.53; H 8.61; N 3.03. Found C 77.27; H 8.71; N 3.08.

EXAMPLE 29

4'-t-Butylphenyl-3-oxo-4-aza-5α-androst-1-ene-17β-carboxylate (29)

Employing substantially the same procedure as described in Example 22, but substituting the guaiacol with 4-t-butylphenol, the titled product 29 was obtained. Mass spec. (MS) calculated, 449.61; observed m/e 449. Anal. calcd. for $C_{29}H_{39}NO_3$, C 77.46; H 8.74; N 3.12. Found C 76.54; H 8.77; N 3.08.

EXAMPLE 30

2'-Fluorophenyl-3-oxo-4-aza-5α-androst-1-ene-17β-carboxylate (30)

Employing substantially the same procedure as described in Example 22, but substituting the guaiacol with 2-fluorophenol, the titled product 30 was obtained. Mass spec. (MS) calculated, 412.529; observed m/e 300 (m-112).

EXAMPLE 31

7β-Methyl-3-oxo-4-aza-5α-androstane-17β-carboxylate (D)

A solution of 5 grams 7β-methyl-3,20-di-oxo-4-aza-5α-pregnane (XI, See following Flowsheet B) in 200 ml. dioxane was treated at 10°-15° C. with 62.5 ml of a hypobromite solution (prepared from 42 g. NaOH in 360 ml. water treated dropwise with 43 g. of bromine at 0° C., total volume—400 ml) over a period of 90 minutes. After stirring for an additional 30 minutes thin layer chromatography (1:1 acetone/methylene chloride, 1% HCOOH) indicated a small amount of starting material still left. More hypobromite solution was added (4.5 ml over 10 minutes) and the mixture stirred for 1.5 hours until TLC indicated starting material was absent. Hydrochloric acid (20%) was added until the mixture was about pH 8. Sodium bisulfite was added until a starch iodide test was negative. The mixture was concentrated until the dioxane was largely removed. Dilute hydrochloric acid was added and the mixture was triturated well and the filtered to yield a precipitate. The precipitate was dried to leave 3.2 g. crude solid.

The solid was recrystallized from hot methanol to yield the above-titled intermediate D, mp. 311°-312° C. Anal. Calc. for $C_{20}H_{29}NO_3\cdot 0.4H_2O$ MW 333.47 (hydrate), Calc. C 70.51; H 9.41; N 4.11; Found: C 70.52; H 9.33; N 4.07.

The following table lists the above compounds made in this invention and their physical properties in terms of the characteristic C-18, C-19 angular methyl groups and other significant proton absorption peaks which characterize and identify the specific molecular structures. The term "Ar" represents an aromatic proton(s).

TABLE

| Compound No. | NMR Data Angular Methyls (ppm) | Miscellaneous (ppm) |
|---|---|---|
| 1 | 0.734,0.874 | 2.907 (N—CH₃), 7.24–7.7,8.59–8.6(pyridyl) |
| 2 | 0.839,0.895 | 3.79(O—CH₃), 6.88–7.18(AR) |
| 3 | 0.807,0.891 | 3.78(O—CH₃) 6.6–7.27(Ar) |
| 4 | 0.793,0.888 | 3.77(O—CH₃) 6.858–6.958(Ar) |
| 5 | 0.844,0.894 6.57,7.09(AR) | 3.77(O—CH₃) |
| 6 | 0.806,0.882 | 3.8(O—CH₃) 6.28(AR) |
| 7 | 0.89 | 1.318(t-Bu) 2.91(N—CH₃) |
| 8 | 0.816,0.888 | 1.2899(t-Bu) 2.91(N—CH₃) |
| 9 | 0.801,0.887 6.96,7.35(AR) | 1.289(t-Bu) |
| 10 | 0.82,0.891 | 2.91(N—CH₃) 7.08–7.19(Ar) |
| 11 | 0.734,0.902 | 7.22–7.78,8.59–8.62(AR) |
| 12 | 0.839,0.911 | 3.79(O—CH₃) 6.91–7.23(Ar) |
| 13 | 0.801,0.902 | 3.778(O—CH₃) 6.59–7.268(Ar) |
| 14 | 0.800,0.920 | 3.777(O—CH₃) 6.863–6.96(Ar) |
| 15 | 0.844,0.911 | 3.778(O—CH₃) 6.578,7.096(Ar) |
| 16 | 0.82,0.92 | 3.8(O—CH₃) |
| 17 | 0.891,0.906 | 1.32(t-Bu) 6.93–7.377(Ar) |
| 18 | 0.819,0.908 | 1.291(t-Bu) 6.845–7.296(Ar) |
| 19 | 0.801,0.903 | 1.298(t-Bu) 6.965,7.354(Ar) |
| 20 | 0.811,0.897 | 3.032–3.061(5-H) |
| 21 | 0.76,0.98 | 7.2607.78(Ar) |
| 22 | 0.85,0.982 | 3.795(O—CH₃) 6.85–7.20(Ar) |
| 23 | 0.812,0.971 | 3.77(O—CH₃) 6.6–7.269(Ar) |
| 24 | 0.806,0.977 | 3.778(O—CH₃),6.86–6.96(Ar) |
| 25 | 0.856,0.983 | 3.783(O—CH₃) 6.80,7.1(Ar) |
| 26 | 0.823,0.974 | 3.80(O—CH₃) 6.278(Ar) |
| 27 | 0.90,0.98 | 1.30(t-Bu) 6.79(C-1),5.78(C-2) |
| 28 | 0.811,0.972 | 1.29(t-Bu) 6.79(C-1),5.8(C-2) |
| 29 | 0.811,0.972 | 1.29(t-Bu) 6.9,7.35(Ar) |
| 30 | 0.832,0.979 | 6.79(C-1).5.80(C-2) 7.08–7.18(Ar) |

FLOWSHEET A

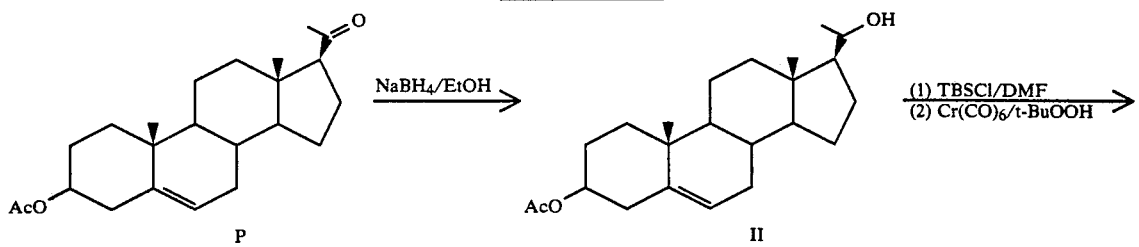

-continued
FLOWSHEET A
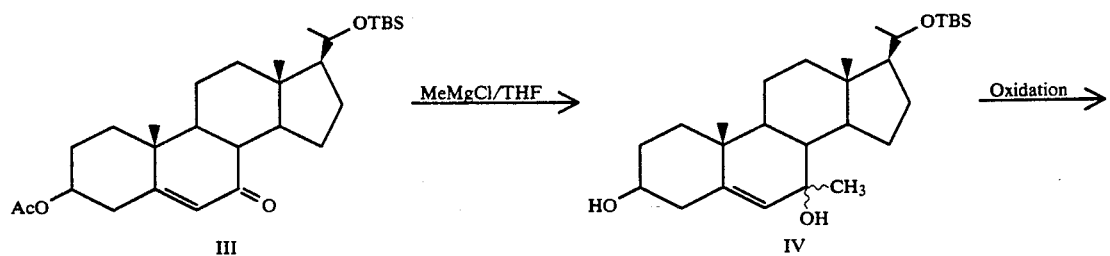
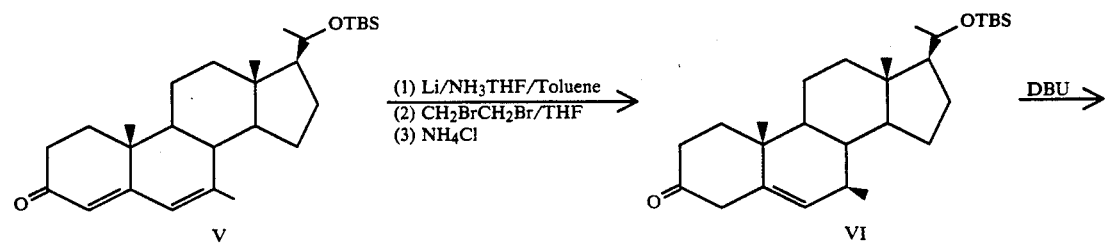
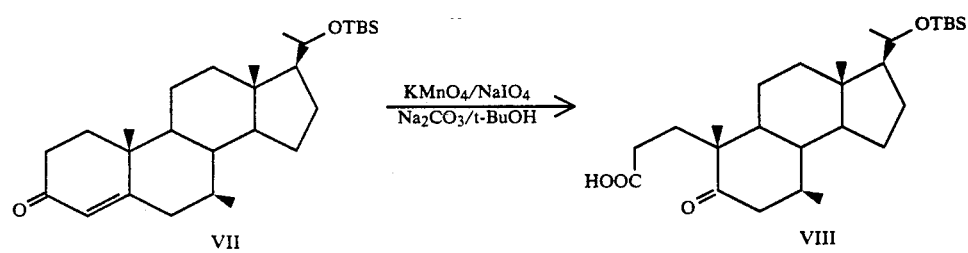
FLOWSHEET B
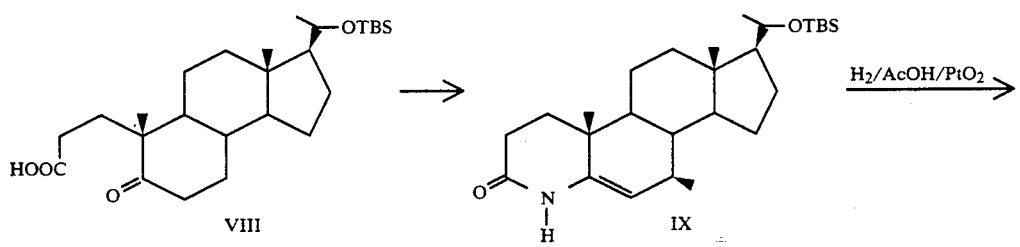
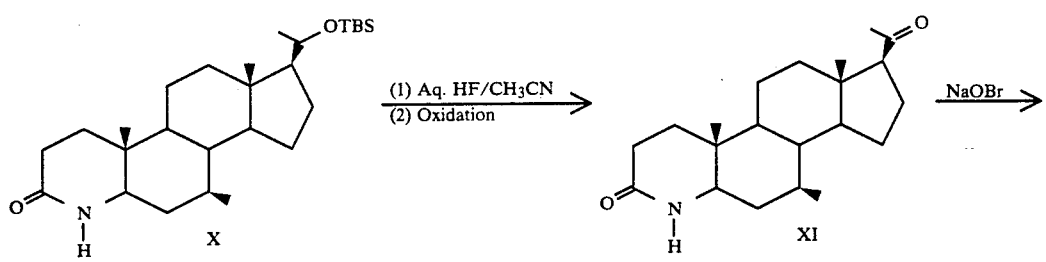
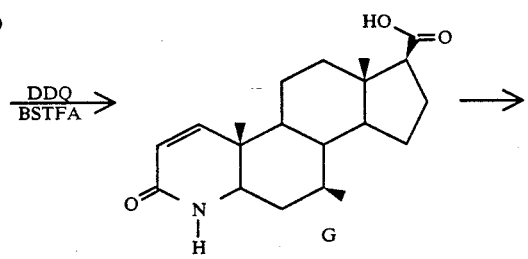

-continued
FLOWSHEET B

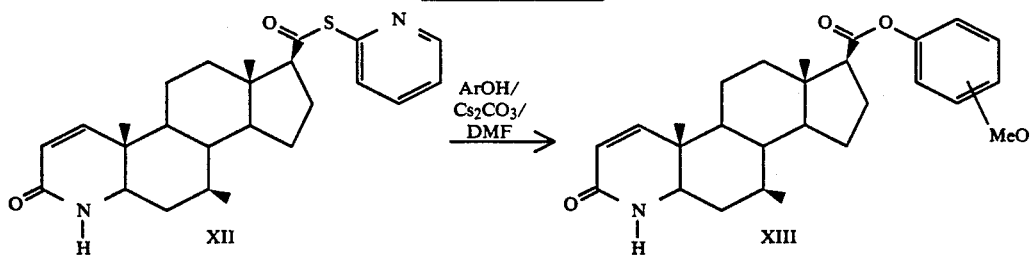

EXAMPLE 31

2'-Methoxyphenyl-7-methyl-3-oxo-4-aza-5α-androstane-17β Carboxylate

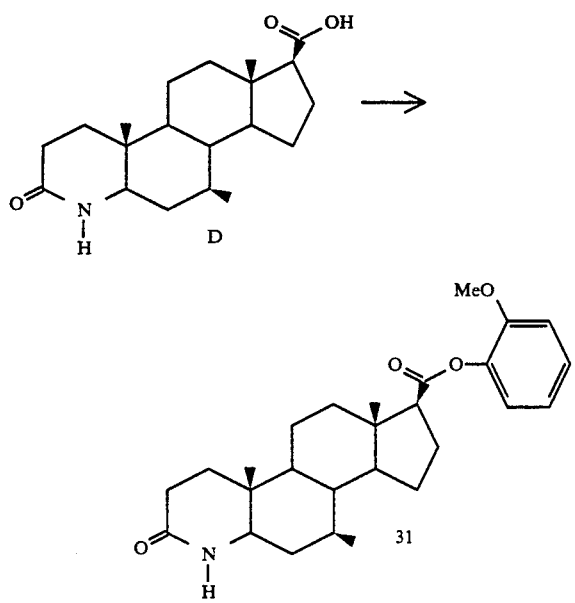

The intermediate XII is reacted with aldrithiol/PPh$_3$ analogously as described above to give the corresponding 2-thiopyridyl ester.

This in turn is reacted with guaiacol, DMF, cesium carbonate, analogously as in Example 12 to yield 2'-methoxyphenyl-7β-methyl-3-oxo-4-aza-5α-androstane-17β-carboxylate (31).

Similarly, using other substituted phenols, other 7β-methyl-aza-steroid-17-substituted phenyl carboxylates can be produced as described herein.

PREPARATION OF THE STARTING MATERIAL D

As seen in the Flowsheets A and B, pregnenolone-3-acetate (P) is first reduced to the alcohol II by sodium borohydride in ethanol at −10° to 0° C. The alcohol II is then protected by a dimethyl-t-butyl silyl (TBS) group in DMF with TBS chloride and imidazole as a base at room temperature. The protected alcohol is then oxidized to the corresponding 5-en-7-one III by treatment with hydrogen t-butyl peroxide and chromium hexacarbonyl in e.g., acetonitrile, at reflux. The 7-methyl group can be introduced at this point by a Grignard reaction using e.g., methyl magnesium chloride in e.g., anhydrous THF at 0° to −10° C. to produce the 7-methyl-7-hydroxy adduct IV. This is then oxidized with e.g. aluminum isopropoxide and cyclohexanone (Oppenauer oxidation conditions) in refluxing toluene solvent to produce the 7-methyl-4,6-dien-3-one V. This in turn is reduced via e.g., metal-ammonia, THF and toluene at −78° C. to selectively yield the 7-beta-methyl-5-en-3-one VI. In the next step the delta-5-double bond is isomerized to the 4-ene by use of DBU (1,8-diazabicylco-[5.4.0]undec-7-ene) in e.g. refluxing tetrahydrofuran (THF) to produce the 7-methyl-4-ene-3-one, VII. The A ring is next cleaved by treatment with e.g. potassium permanganate, sodium periodate in t-butyl alcohol at 80° C. to produce the corresponding seco-acid VII.

Treatment of the seco-acid with ammonium acetate in glacial acetic acid at 120° C. yields e.g., the 7-methyl-4-aza-pregn-5-en-3-one IX. This is turn is selectively reduced with e.g., PtO2, to remove the 5-double bond to produce the 5α-hydrogen compound X. The TBS protecting group is next removed by aqueous HF in acetonitrile at room temperature and then oxidized by tetrapropylammonium perruthenate/4-methylmorpholine N-oxide in methylene chloride at room temperature to yield the 17-acetyl compound XI, mp. 215°–217° C. This is treated with sodium hypobromite/sodium hydroxide solution in dioxane at 10°–15° C. to form the starting intermediate 17-carboxylic acid D, mp. 311°–312° C. This is then used as described above to make the 2-thiopyridyl ester and the resulting azasteroidal phenyl carboxylates.

The 1,2-double bond in the A ring can be introduced into D by DDQ oxidation (see procedure in U.S. Pat. No. 5,084,574) to produce G, mp 328°–330° C. Formation of the 2-thiopyridyl intermediate XII, analogously as described above, and reaction with a methoxy substituted phenols as described above produces the corresponding phenyl carboxylates, XIII.

What is claimed is:

1. A compound of the formula:

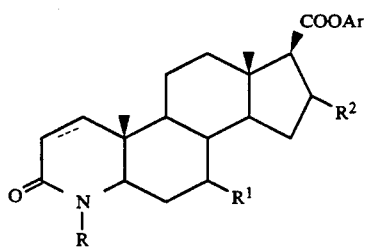

wherein:
the dashed line can represent a double bond when present;
R is selected from hydrogen, methyl, ethyl;
R$^1$ can be:

1) oxo;
2) alpha-hydrogen and beta-hydrogen or a beta-substituent selected from: $C_1$–$C_4$ alkyl, $C_2$–$C_4$ alkenyl, $CH_2COOH$, hydroxy, carboxy, COOC-$_1$–$C_4$ alkyl esters; $OCONR^3R^4$, where $R^3$ and $R^4$ are independently H, $C_1$–$C_4$ alkyl, phenyl, benzyl, and $R^3$ and $R^4$ together with the nitrogen can form a ring selected from the group consisting of piperidinyl, pyrrolidinyl and morpholinyl, $OC_1$–$C_4$ alkyl, $OC_3$–$C_6$ cycloalkyl, $OCOCH_3$, halo, hydroxy $C_1$–$C_2$ alkyl, halo $C_1$–$C_2$ alkyl, trifluoromethyl, $C_3$–$C_6$ cycloalkyl;
3) =CH—R' where R' is H, $C_1$–$C_4$ alkyl;
4) spiro:

where R' is H, $C_1$–$C_4$ alkyl;
$R^2$ is independently selected from the following alpha and beta substituents: hydrogen, $C_1$–$C_6$ alkyl; and
Ar is a $C_6$–$C_{10}$ aromatic ring substituted with one or more of $C_1$–$C_4$ alkyl, $C_1$–$C_5$ alkoxy, or halo;
and pharmaceutically acceptable salts and esters thereof.

2. The compound of claim 1 wherein said Ar is substituted phenyl.

3. The compound of claim 1 wherein $R^1$ is H or $C_1$–$C_4$ alkyl.

4. The compound of claim 1 wherein said R is H or $CH_3$ and $R^2$ is H.

5. A compound as claimed in claim 1 selected from the group consisting of:
2'-Methoxyphenyl-3-oxo-4-methyl-4-aza-5α-androstane-17β-carboxylate;
3'-Methoxyphenyl-3-oxo-4-methyl-4-aza-5α-androstane-17β-carboxylate;
4'-Methoxyphenyl-3-oxo-4-methyl-4-aza-5α-androstane-17β-carboxylate;
2',5'-dimethoxyphenyl-3-oxo-4-methyl-4-aza-5α-androstane-17β-carboxylate;
3',4',5'-trimethoxyphenyl-3-oxo-4-methyl-4-aza-5α-androstane-17β-carboxylate;
2'-t-Butylphenyl-3-oxo-4-methyl-4-aza-5α-androstane-17β-carboxylate;
3'-t-Butylphenyl-3-oxo-4-methyl-4-aza-5α-androstane-17β-carboxylate;
4'-t-Butylphenyl-3-oxo-4-methyl-4-aza-5α-androstane-17β-carboxylate;
2'-Fluorophenyl-3-oxo-4-methyl-4-aza-5α-androstane-17β-carboxylate;
2'-Methoxyphenyl-3-oxo-4-aza-5α-androstane-17β-carboxylate;
3'-Methoxyphenyl-3-oxo-4-aza-5α-androstane-17β-carboxylate;
4'-Methoxyphenyl-3-oxo-4-aza-5α-androstane-17β-carboxylate;
2',6'-Dimethoxyphenyl-3-oxo-4-aza-5α-androstane-17β-carboxylate;
3',4',5'-trimethoxyphenyl-3-oxo-4-aza-5α-androstane-17β-carboxylate;
2'-t-Butylphenyl-3-oxo-4-aza-5α-androstane-17β-carboxylate;
3'-t-Butylphenyl-3-oxo-4-aza-5α-androstane-17β-carboxylate;
4'-t-Butylphenyl-3-oxo-4-aza-5α-androstane-17β-carboxylate;
2'-Fluorophenyl-3-oxo-4-aza-5α-androstane-17β-carboxylate;
2'-Methoxyphenyl-3-oxo-4-aza-5α-androst-1-ene-17β-carboxylate;
3'-Methoxyphenyl-3-oxo-4-aza-5α-androst-1-ene-17β-carboxylate;
4'-Methoxyphenyl-3-oxo-4-aza-5α-androst-1-ene-17β-carboxylate;
2',6'-dimethoxyphenyl-3-oxo-4-aza-5α-androst-1-ene-17β-carboxylate;
3',4',5'-trimethoxyphenyl-3-oxo-4-aza-5α-androst-1-ene-17β-carboxylate;
2'-t-Butylphenyl-3-oxo-4-aza-5α-androst-1-ene-17β-carboxylate;
3'-t-Butylphenyl-3-oxo-4-aza-5α-androst-1-ene-17β-carboxylate;
4'-t-Butylphenyl-3-oxo-4aza-5α-androst-1-ene-17β-carboxylate; and
2'-Fluorophenyl-3-oxo-4-aza-5α-androst-1-ene-17β-carboxylate.

6. The compound, 7β-methyl-3-oxo-4-aza-androstane-17β-carboxylic acid (D).

7. The compound, 7β-methyl-3-oxo-4-aza-androst-1-ene-17β-carboxylic acid (G).

8. A pharmaceutical composition comprising a therapeutically effective amount of the compound of claim 1 in a pharmaceutically acceptable vehicle therefor.

* * * * *